(12) United States Patent
Loggie

(10) Patent No.: US 7,008,395 B1
(45) Date of Patent: Mar. 7, 2006

(54) MULTI-LUMEN CATHETER SYSTEM USED IN A BLOOD TREATMENT PROCESS

(75) Inventor: Brian W. Loggie, Fort Worth, TX (US)

(73) Assignee: Wake Forset University Health Sciences, Winston-Salem, NC (US)

( * ) Notice: Subject to any disclaimer, the term of this patent is extended or adjusted under 35 U.S.C. 154(b) by 767 days.

(21) Appl. No.: 09/676,363

(22) Filed: Sep. 29, 2000

Related U.S. Application Data

(63) Continuation of application No. 08/931,579, filed on Sep. 16, 1997, now Pat. No. 6,126,631, which is a continuation of application No. 08/584,716, filed on Jan. 11, 1996, now abandoned, which is a continuation of application No. 08/222,297, filed on Apr. 4, 1994, now abandoned.

(51) Int. Cl.
*A61M 37/00* (2006.01)
*A61M 3/00* (2006.01)

(52) U.S. Cl. .................. 604/6.16; 604/43; 604/264

(58) Field of Classification Search ................ 604/4–6, 604/27, 43, 53, 264, 280, 6.16, 258, 283–284, 604/39, 93.01, 272, 523, 537, 533–534, 540–541, 604/543–544; 138/111–118
See application file for complete search history.

(56) References Cited

U.S. PATENT DOCUMENTS

| | | | |
|---|---|---|---|
| 3,800,799 A | 4/1974 | McWhorter | ................. 604/283 |
| 4,072,146 A | 2/1978 | Howes | |
| 4,134,402 A | 1/1979 | Mahurkar | |

(Continued)

FOREIGN PATENT DOCUMENTS

WO 9526763 10/1995

OTHER PUBLICATIONS

"Analysis of venous access for therapeutic plasma exchange in patients with neurological disease", Grishaber, et al., J. Clin Apheresis, 7:119-123, 1992.

(Continued)

*Primary Examiner*—Patricia Bianco
*Assistant Examiner*—Leslie R. Deak
(74) *Attorney, Agent, or Firm*—Donald R. Riper, Jr.; Dann, Dorfman, Herrell & Skillman, P.C.

(57) ABSTRACT

A catheter system facilitates blood treatments such as apheresis that require simultaneous withdrawal and return of blood to a patient at high flow rates. A multi lumen catheter has an external coupling device connected to a pump and blood treatment device. All of the lumens are designed to be used in the blood treatment process. The catheter includes two or more lumens for withdrawing blood and a return lumen for returning treated blood. The combined flow resistance of the withdrawal lumens is less than or equal to the flow resistance of the return lumen so that the flow rate of blood through the withdrawal lumens does not require a pressure differential sufficient to collapse the lumens. High flow rates are achievable through the catheter by using a pair of withdrawal lumens instead of a single, large withdrawal lumen. The lumens may be used for general medical use when the catheter system is not being used for exchange treatments. To help reduce mixing of blood between the withdrawal lumens and the return lumens, the catheter has a beveled distal end for angling the distal ends of the withdrawal lumens away from the distal end of the return lumen. A catheter cutting tool is provided for cutting the catheter to a selected length and for providing a precise beveled distal end.

12 Claims, 5 Drawing Sheets

U.S. PATENT DOCUMENTS

| | | | |
|---|---|---|---|
| 4,385,631 A | 5/1983 | Uthmann | |
| 4,406,656 A * | 9/1983 | Hattler et al. | 604/523 |
| RE31,873 E | 4/1985 | Howes | |
| 4,543,087 A | 9/1985 | Sommercorn et al. | |
| 4,568,329 A | 2/1986 | Mahurkar | |
| 4,583,968 A | 4/1986 | Mahurkar | |
| 4,592,340 A | 6/1986 | Boyles | 128/1 |
| 4,619,643 A | 10/1986 | Bai | |
| 4,692,141 A | 9/1987 | Mahurkar | |
| 4,705,507 A | 11/1987 | Boyles | 604/101 |
| 4,772,261 A | 9/1988 | Von Hoff et al. | 604/51 |
| 4,772,268 A | 9/1988 | Bates | |
| 4,795,439 A | 1/1989 | Guest | |
| 4,808,156 A | 2/1989 | Dean | 604/43 |
| 4,816,221 A | 3/1989 | Harvey et al. | 604/283 |
| 4,822,345 A | 4/1989 | Danforth | |
| 4,838,881 A * | 6/1989 | Bennett | 604/523 |
| 4,894,057 A | 1/1990 | Howes | 604/280 |
| 4,895,561 A | 1/1990 | Mahurkar | |
| 4,925,452 A | 5/1990 | Melinyshyn et al. | 604/284 |
| 4,995,865 A | 2/1991 | Gahara et al. | |
| 4,997,424 A | 3/1991 | Little | |
| 5,020,543 A | 6/1991 | Rothenberg et al. | 128/760 |
| 5,057,073 A | 10/1991 | Martin | |
| 5,059,170 A | 10/1991 | Cameron | 604/283 |
| 5,069,662 A | 12/1991 | Bodden | 604/4 |
| 5,122,114 A | 6/1992 | Miller et al. | 604/49 |
| 5,149,330 A | 9/1992 | Brightbill | |
| 5,160,325 A * | 11/1992 | Nichols et al. | 604/247 |
| 5,188,606 A | 2/1993 | Maloney et al. | |
| 5,195,962 A | 3/1993 | Martin et al. | |
| 5,197,951 A | 3/1993 | Mahurkar | |
| 5,207,643 A | 5/1993 | Davis | 604/80 |
| 5,221,255 A | 6/1993 | Mahurkar et al. | |
| 5,221,256 A | 6/1993 | Mahurkar et al. | |
| 5,250,041 A | 10/1993 | Folden et al. | 604/284 |
| 5,330,460 A | 7/1994 | Moss et al. | |
| 5,374,245 A | 12/1994 | Mahurkar | |
| 5,378,230 A * | 1/1995 | Mahurkar | 604/43 |
| 5,382,238 A | 1/1995 | Abrahamson et al. | |
| 5,395,316 A * | 3/1995 | Martin | 604/43 |
| 5,403,291 A | 4/1995 | Abrahamson | |
| 5,405,321 A | 4/1995 | Reeves | 604/283 |
| 5,800,408 A | 9/1998 | Strauss et al. | |
| 5,836,912 A | 11/1998 | Kusleika | |
| 5,911,706 A | 6/1999 | Estabrook et al. | |
| 5,931,829 A | 8/1999 | Burbank et al. | |
| 5,947,953 A * | 9/1999 | Ash et al. | 604/508 |
| 6,126,631 A | 10/2000 | Loggie | |
| 6,146,354 A * | 11/2000 | Beil | 604/28 |

OTHER PUBLICATIONS

"Subclavian vein catheterization for apheresis access", Spindler, J. Clin Apheresis, 1:202-205, 1983.

"Central venous access for apheresis access", Thompson, L., J. Clin Apheresis, 7:154-157, 1992.

"Pulmonary hypertension", Honey, Oxford Textbook of Medicine, vol. 2, Section 13.241.

* cited by examiner

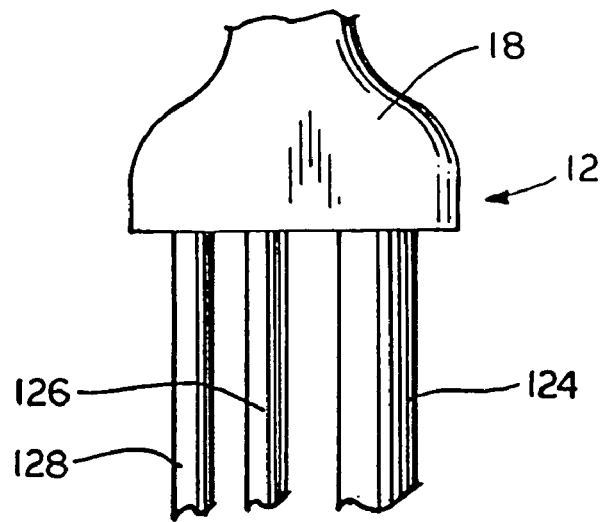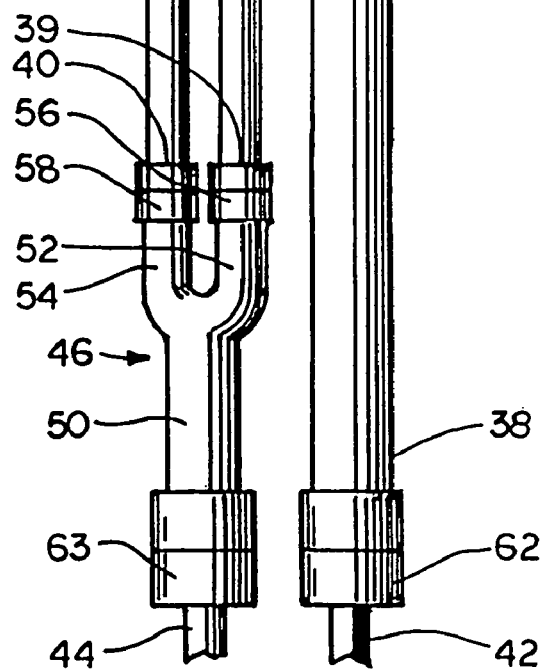
FIG. 2

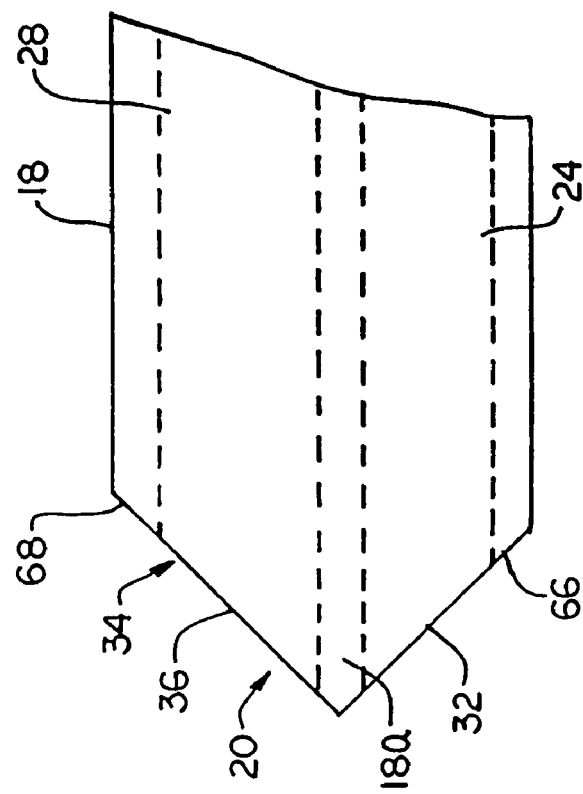
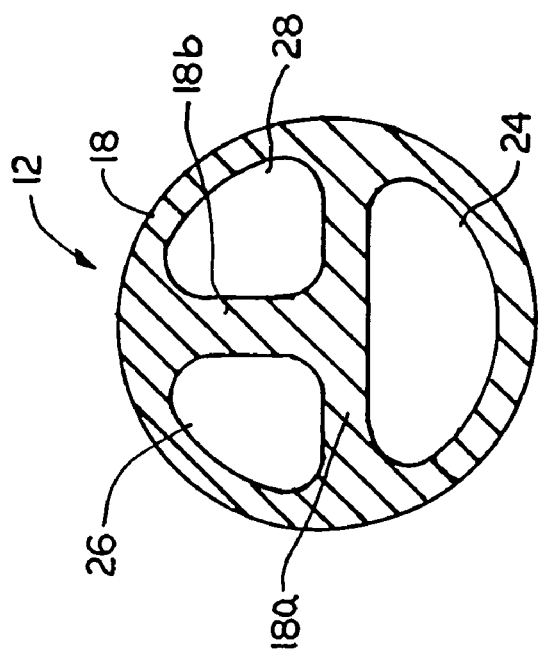

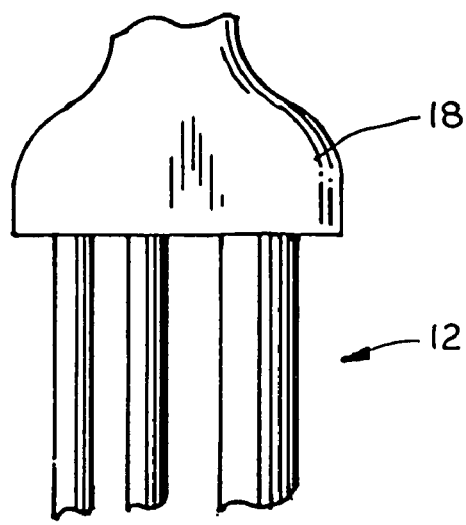
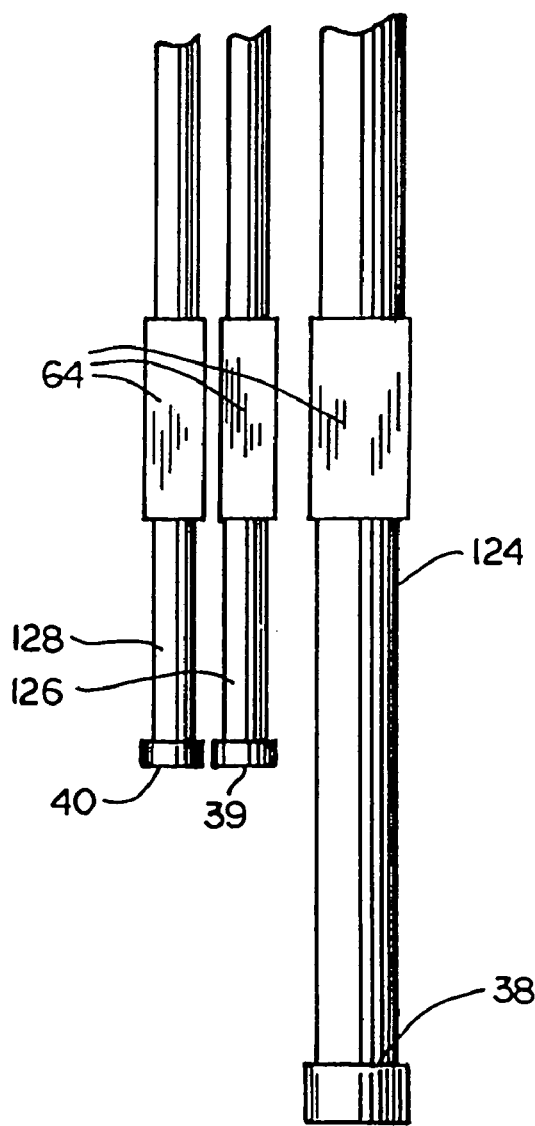
FIG. 4

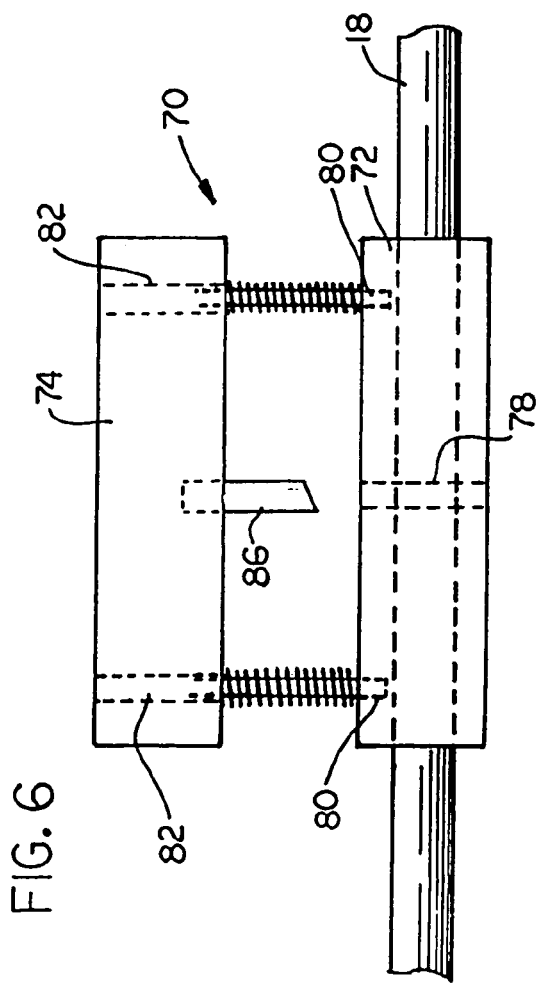
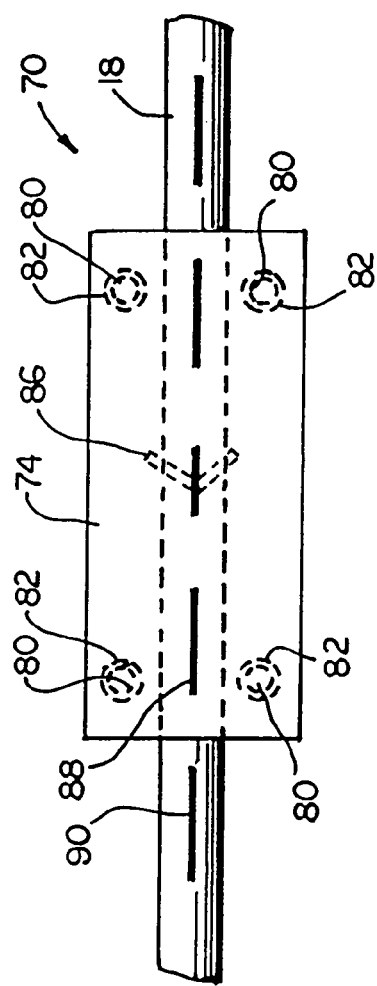
FIG. 6
FIG. 7

MULTI-LUMEN CATHETER SYSTEM USED IN A BLOOD TREATMENT PROCESS

RELATED APPLICATIONS

This application is a continuation of U.S. application Ser. No. 08/931,579, filed Sep. 16, 1997, now U.S. Pat. No. 6,126,631 which is a continuation of U.S. application Ser. No. 08/584,716, filed Jan. 11, 1996, abandoned, which is a continuation of U.S. application Ser. No. 08/222,297, filed Apr. 4, 1994, abandoned, such applications being incorporated herein by reference.

FIELD OF INVENTION

The present invention relates generally to multi-lumen catheter systems and more particularly to triple lumen catheter systems that provide for simultaneous withdrawal and return of blood to a patient undergoing a blood treatment process.

BACKGROUND OF THE INVENTION

Current medical treatments have increased the technical demands placed on catheter systems designed for central venous vascular access in patients. The present invention solves a problem that arises as the result of new medical treatment strategies requiring the combined use of certain blood treatment processes such as apheresis and sophisticated supportive care such as autologous bone marrow transplant (BMT).

According to Grishaber, J. E. et al, "Analysis of venous access for therapeutic plasma exchange in patients with neurological disease", *J. Clin. Apheresis* 7:119–123, 1992, apheresis service (described below) using a central venous catheter is most efficiently done with a dual lumen catheter. Other supportive treatments such as BMT optimally require a triple lumen device, according to Moosa, H. H. et. al., "Complications of indwelling central venous catheters in bone marrow transplant recipients", *Surg. Gynecol. Obstet.* 172:275–279, 1991. The current choices that a clinician has available are to either use one catheter type and thus deliver one phase of therapy inefficiently, or to use two catheters and subject the patient to additional surgical procedures, risks, discomfort and cost.

Apheresis (called also pheresis) is a blood treatment process involving separation of blood elements that can remove soluble compounds or cellular elements from the circulation. Deisseroth et al., "Use of blood and blood products", *Cancer: principles and practice of oncology*, Devita, V. T. Jr. et al editors, Philadelphia: J. B. Lippincott Company 1989, p. 2045–2059. Blood is withdrawn from a donor, a portion (plasma, leukocytes, platelets, etc) is separated and retained, and the remainder is retransfused to the donor *Dorland's illustrated medical dictionary*, 27th Edition, W. B. Saunders, Philadelphia, 1988. Specific cell types such as circulating pluripotent stem cells (peripheral stem cells) for use in autologous BMT are harvested using apheresis techniques (leukapheresis).

To pump blood from the patient through the withdrawal lumen, a vacuum must be placed on the withdrawal lumen by a system pump. As the vacuum is increased so as to increase the withdrawal flow rate, the withdrawal lumen tends to collapse. In some cases, this tendency to collapse at low pressures or flow rates prohibits use of a many catheters for apheresis Grishaber et al., supra and Spindler, J. S., "Subclavian vein catheterization for apheresis access", *J. Clin. Apheresis* 1:202–205, 1983. In contrast, the return lumen is placed under a positive pressure by the system pump to pump blood into the patient, and accordingly, the return lumen is not susceptible to collapse.

Certain prior art tunnelled dual-lumen catheters, such as the Hickman dual lumen catheter, can be used to simultaneously input and output blood to a patient at minimally adequate flow rates. However, these dual-lumen catheters are still susceptible to collapse at more optimal, higher flow rates. Grishaber et al found that additional access was required to complete 27% of procedures when using the Hickman dual lumen catheter and 67% for triple lumen catheters (Arrow International triple-lumen 7 French catheter) and stated in reference to venous access for plasma exchange that they "believe that the difficulties they pose preclude their use for routine procedures." This contributes significantly to the amount of time required to perform these services and increases the cost of these services.

Other dual lumen short-term (non-tunnelled) catheters are larger and stiffer have been designed primarily for dialysis and can accommodate the demands of apheresis. However, these are designed for short-term placement (days to weeks). For example, it is recommended that the dual lumen Mahurkar catheter (Quinton Instrument Company, Seattle, Wash.) be replaced every 3 weeks when used in the subclavian or jugular vein. These catheters are generally recommended for exclusive use for the blood treatment process (see Spindler, supra), and have short stiff external lumen branches that are often uncomfortable and somewhat difficult to dress. Thompson, L., "Central venous access for apheresis access," *J. Clin. Apheresis* 7:154–157, 1992 and Grishaber, supra. They are therefore not considered satisfactory for longer term general use as for BMT (generally weeks to months). A dual lumen catheter designed for dialysis and long-term use is the PermCath (Quinton). This catheter can sustain the necessary flow rates for apheresis service but is not without problems. This large, stiff, silicone rubber catheter is oval (4.9 mm×2.8 mm, OD) and requires a specialized introducer to minimize the risk of air embolism at the time of venous placement. It has a specialized cuff for long term implantation in subcutaneous tissue. It is recommended for internal jugular placement rather than subclavian or external jugular because of the size and stiffness and possibility for complications. Catheter care and comfort thus pose a problem as for similar design short-term dialysis catheters and only 2 lumens are available for general use. Thompson, supra.

BMT is being used increasingly in the supportive care relating to therapy of an increasing array of cancers, including breast cancer. Patients are given intense treatment that is designed to be maximally effective against their cancer with the main toxicity being potentially lethal bone marrow suppression. For autologous BMT, the peripheral stem cells harvested earlier from the patient by apheresis are returned to that patient to repopulate the bone marrow elements depleted by treatment. Patients then require intense supportive care until bone marrow recovery is complete. Optimal vascular access is important for this critical phase of treatment. Current treatment protocols often require administration of multiple drugs and support with intravenous fluids, antibiotics, hyperalimentation, growth factors, and blood products. For efficient administration of these multiple substances, often for many weeks, the use of multiple catheter lumens is optimal. This can be accomplished with dual lumen catheter access systems but is more difficult and requires "juggling" by health care workers of the multiple infusions, medications, and blood draws. Thus, the implantation of catheter systems having three or more lumens is optimal for vascular venous access to facilitate long term intensive medical treatments. Grishaber et. al., supra. For patients undergoing BMT, triple lumen indwelling catheters are generally recommended for vascular access. Moosa et al., supra.

However, for those patients that also require apheresis service, prior art triple-lumen catheters cannot sustain the high flow rates into and out of a patient required for these blood treatment processes and are not recommended for use. The use of a dual lumen Hickman catheter, a tunnelled catheter in common use, is reported but is associated with a significant rate of failure due to failure of the draw port. Even when functional, the flow exchange flow rates are minimal and limiting for this type of catheter and increase the amount of time required to perform an apheresis service and the amount of attention required by personnel administering the service. Another important consideration is that multiple treatments are usually necessary. In order to complete an apheresis blood treatment session in a timely manner, blood must be withdrawn and returned to a patient at an adequate flow rate. For example, stem cell harvest typically requires that nine liters of blood be exchanged in preferably three hours or less. Blood flow rates of 60 cc/min or higher through a catheter are required to provide for such an exchange rate of blood. In addition, the roller pumps in use result in pulsatile flow rather than constant flow and pressures. These relatively high flow rates cannot be approached or sustained by many prior art tunnelled dual lumen catheters in current general use. Applicant is unaware of any tunnelled triple or quadruple lumen catheters that can be used effectively for apheresis. These catheters are soft and flexible with limited internal lumen diameters. The withdrawal lumen used to withdraw blood from the patient is particularly susceptible to collapse.

SUMMARY OF THE INVENTION

The current invention provides a specialized multilumen (3 or 4 lumen) catheter system designed to allow the possibility of efficient apheresis or other specialized blood treatment processes by using all lumens. These lumens are engineered to facilitate the exchange treatment process by matching flow resistance between designated inflow and outflow lumens. This catheter system is designed to support the high exchange flow rates as required by apheresis service at low pressures without collapse of the withdrawal lumen (s) and is also designed for placement as a long-term tunnelled catheter that provides independent multiple lumens for long term general vascular venous access for use in supportive treatments such as BMT.

The catheter system of the present invention allows for simultaneous withdrawal and return of equal amounts of blood or fluid to a patient at high flow rates. The high flow rate sustainable by the catheter system permits a patient to undergo specialized blood treatments such as apheresis in a timely fashion and can also be used in the manner of a conventional triple-lumen catheter for other general treatment purposes, such as supportive care for BMT. The catheter system of the present invention includes a specialized multilumen catheter with coupling device that is capable of connection to a conventional pump and blood treating device in the usual way.

The catheter has three or more lumens of which two or more can be joined together for removing blood from the patient and of which at least one lumen is provided for returning the processed blood to the patient. The lumens coupled together for withdrawal have a combined flow resistance substantially less than or equal to the flow resistance of the return lumen. In this manner, the potential for collapse of the withdrawal lumens at the desired flow rates is eliminated or substantially reduced. All lumens are used in the blood treatment process, enhancing the efficiency of the catheter.

Multiple lumens are provided for blood withdrawal with an intervening septum instead of a single larger lumen because this architecture provides greater resistance to collapse due to the higher ratio of wall thickness to lumen surface area and the shorter span of outer catheter wall between any two supporting septum walls.

The preferred embodiment of the invention is a triple lumen catheter with two of the lumens merged together by an external coupler. The pair of withdrawal lumens and external coupler together form a withdrawal lumen branch. The external coupler has two auxiliary branches that attach to the withdrawal lumens and a single main branch that is conventionally connected with a tube leading to the system pump and blood treatment device. The external coupler is designed to merge withdrawal flows so that the pressure differential necessary to create the desired flow rate is not of a magnitude sufficient to collapse the lumens.

In one embodiment, the catheter is provided with a beveled distal end to help reduce two-way flow disturbance and mixing of fluids or blood elements flowing into and out of the patient. The beveled distal end of the catheter has a first surface and second surface that are angled generally away from one another. The distal ends of the withdrawal lumens are disposed flush on one surface while the distal end of the return lumen is disposed flush on the other surface. This results in the distal end of the withdrawal lumens and the distal end of the return lumen being angled away from one another. Accordingly, blood delivered into the patient at the distal end of the return lumen is not immediately drawn into the withdrawal lumens.

To provide for precise beveling of the distal end and the catheter tube, a catheter cutting tool is provided as a part of the catheter system. The catheter cutting tool is positionable about the catheter and has a blade that is movable between a non-cutting position and a cutting position. Markings are provided on the catheter tube's outer surface and on the cutting tool to allow for proper and precise alignment of the cutting tool to ensure precise cutting of the catheter.

BRIEF DESCRIPTION OF THE DRAWINGS

FIG. 2 is a side view of the catheter showing the catheter coupled to the apheresis tubes.

FIG. 3 is a cross-sectional view showing the catheter tube.

FIG. 4 is a side view of the catheter with the external coupler and apheresis tubes removed.

FIG. 5 is a side view showing the distal end of the catheter.

FIG. 6 is a side view of the catheter cutting tool positioned above the catheter.

FIG. 7 is a top view of the catheter cutting tool positioned about the catheter.

DETAILED DESCRIPTION OF THE PREFERRED EMBODIMENT

Figure 1:
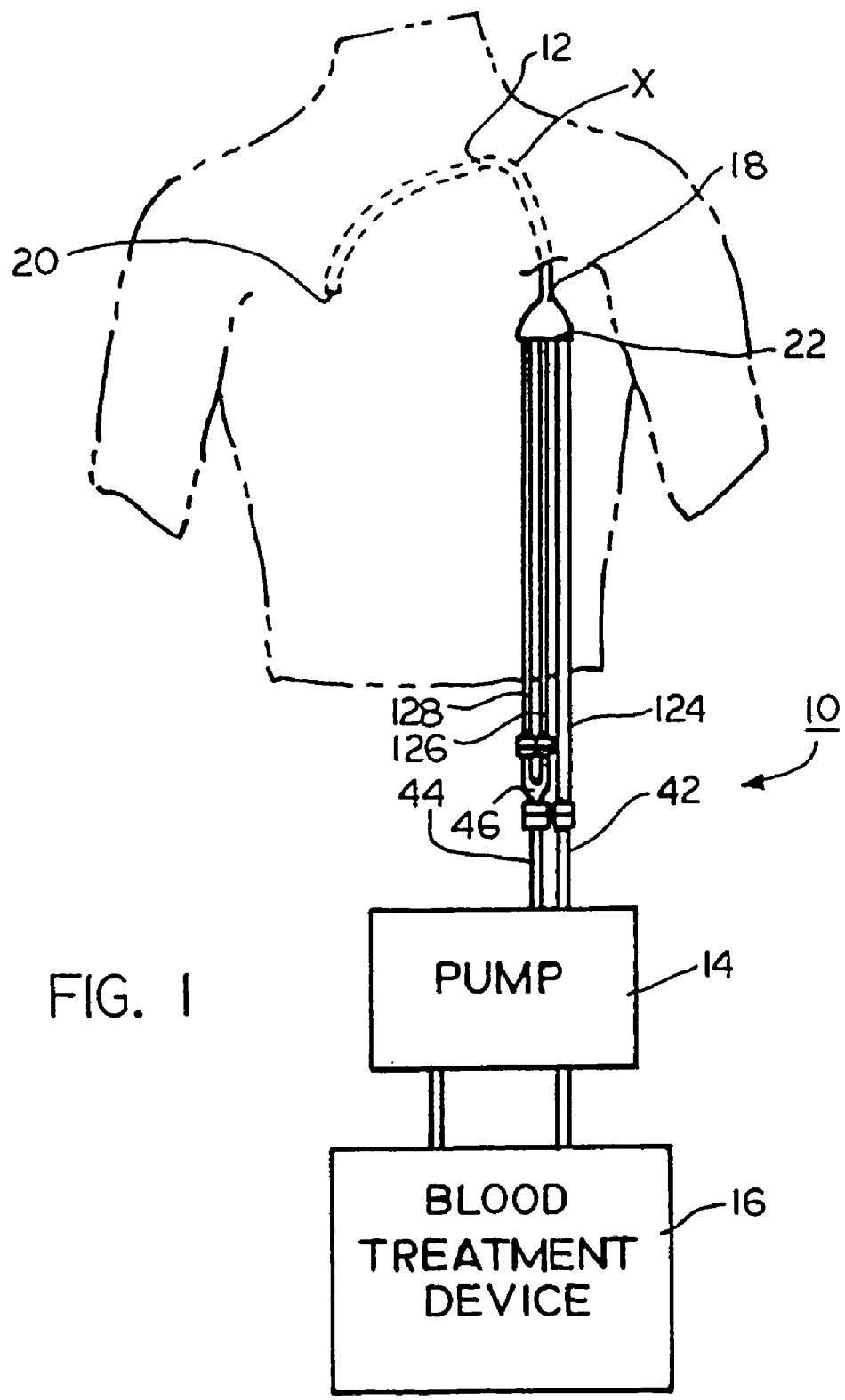
FIG. 1 is an overall schematic view of the catheter system.

Referring to the drawings, the triple-lumen catheter system of the present invention is indicated generally by the numeral 10. Multi-lumen catheter system 10 is designed to permit the simultaneous withdrawal and return of equal amounts of blood to a patient at high flow rates. The high blood flow rates sustainable by catheter system 10 permit catheter system 10 to be effectively used for blood treatments such as apheresis including stem cell harvest and also permit its' use as a multi-purpose catheter such as for BMT purposes.

As shown in FIG. 1, catheter system 10 includes a multi-lumen catheter 12 and coupling device 46. Multi-lumen catheter 12 is insertable by conventional means into the circulatory system of a patient and pump 14 acts to simultaneously withdraw and return blood to the patient. Coupled to pump 14 is blood treatment device 16 which treats blood withdrawn from a patient. As pump 14, blood treatment device 16, and the connecting tubing 44 and 42 are conventional, a detailed description of these is not deemed necessary. The blood treatment device 16 may be an apheresis machine such as for pluripotent stem cell harvest, or any other suitable device. The present invention is particularly directed to multi-lumen catheter 12 and its combination in catheter system 10.

Multi-lumen catheter 12 includes an elongated catheter tube 18 having a distal end 20 and a proximal end 22. Attached to catheter tube 18 are a plurality of external lumens 124, 126, 128, as shown in FIG. 2, that act as conduits for withdrawing and delivering blood or fluids from and to the patient. External lumens 124, 126, and 128 connect to make continuous paths with the lumens 24, 26, 28 shown in FIG. 3 of the catheter tube 18. As shown in FIG. 3, septums 18a and 18b extend between and separate lumens 24–28. Septums 18a and 18b provide support for catheter tube 18 and help prevent lumens 24–28 from collapsing when they are placed under vacuum or pressure by the action of pump 14 in passing blood or fluid therethrough.

Catheter tube 18 and lumens 24–28 passing therethrough are soft and pliable to facilitate atraumatic insertion into a patient. In the preferred embodiment, catheter tube 18 is less than size 14 French diameter facilitating percutaneous introduction into the venous system via the subclavian vein route, a standard procedure for insertion used with a large number of catheters and devices. A fibrous cuff 19 is attached near to the proximal part of elongated catheter tube 18. This is a standard feature for a tunnelled indwelling catheter which allows for tissue ingrowth to secure the catheter and to prevent bacterial migration. The cuff material can be made of any suitable biomedical material. The materials for making catheter tube 18 are any biomedical polymer suitable for forming a vascular catheter such as silicone, polyurethane and polyethylene.

Lumens 24, 26, 28 and 124, 126, 128 include return lumens 24, 124 and withdrawal lumens 26, 126 and 28, 128. Return lumens 24, 124 function to deliver treated blood to the patient, and withdrawal lumens 26, 126 and 28, 128 form a catheter withdrawal lumen branch for withdrawing blood from the patient. Lumens 24–28 have distal ends 32–36 disposed at the distal end of catheter tube 18, and lumens 124, 126, and 128 have proximal ends 38, 39, 40.

Return lumen 124 and withdrawal lumens 126 and 128 are connected to pump 14 and blood treatment device 16 through return apheresis tube 42 and withdrawal apheresis tube 44. A conventional catheter connector 62 connects the proximal end 38 of return lumen 24 to apheresis tube 42. To connect withdrawal lumens 26 and 28 to apheresis tube 44, an external coupler device 46 is used.

As shown in FIG. 2, external coupler device 46 forms a portion of the withdrawal lumen branch of catheter 12 and functions to merge withdrawal lumens 126 and 128 to provide easy connection with withdrawal apheresis tube 44. External coupler 46 includes a main branch 50 and auxiliary branches 52 and 54 which extend from one end of main branch 50. In the preferred embodiment, external coupler 46 forms a general "Y-shape." In other embodiments, external coupler 46 could also form a general "T-shape." Auxiliary branches 52 and 54 are connected to the proximal ends 39 and 40 of withdrawal lumens 126 and 128, respectively. Conventional type catheter connectors 56 and 58 are used to connect auxiliary branches 52 and 54 to the withdrawal lumens 126 and 128, respectively. Likewise, a catheter connector 63 connects main branch 50 to withdrawal apheresis tube 44.

Lumens 24, 26, 28 are designed so that the flow resistance for withdrawing blood from the patient through the withdrawal lumens 26 and 28 is less than or equal to the flow resistance of the return flow through return lumen 24. To provide for clinically necessary flow rates out of and into the patient with a pressure differential that does not cause collapse of the withdrawal lumens, the combined flow resistances or characteristics of the withdrawal lumens 26 and 28 for the withdrawal path is matched with the flow resistance through return lumen 24 for the return path.

The shape of lumens 24, 26, 28 is one factor determining flow resistance. A cross-sectional view showing the shapes of the lumens 24–26 is depicted in FIG. 3. Lumens 24, 26, 28 should preferably be shaped to maximize the size of lumens 24, 26, 28 in relation to the external wall of catheter tube 18. In addition, lumens 24, 26, 28 should not have any sharp angles that could enhance stasis and clotting within lumens 24, 26, 28. Alternative embodiments of catheter 12 can be designed that have lumens of various sizes and shapes. Also, the return path can be split into two lumens, like the withdrawal path. That is, the catheter tube may have four lumens, if desired. Although the lumens of alternative embodiments can be sized and shaped differently, the combined flow resistances of the withdrawal path must be less than or substantially equal to the flow resistance of the return path.

Because external coupler device 46 forms a portion of withdrawal lumen branch, external coupler 46 is also sized so that its flow resistance is less than or matches the flow resistance of external return lumen 124. In particular, auxiliary branches 52 and 54 of external coupler 46 have a flow resistance which matches the flow resistance of external withdrawal lumens 126 and 128, while main branch 50 of external coupler 46 has a flow resistance which is less than or equals the flow resistance of the external return lumen 124. Accordingly, the flow resistance of withdrawal lumen branch is less than or equal to the flow resistance of return lumen 24 so that the pressure differential necessary to create the desired flow rates will not collapse the withdrawal lumens. Alternative embodiments of external coupler device 46 could allow for damping of pressure surges transmitted from pump 14.

Referring to FIG. 4, safety occluders 64 can be placed on external lumens 124–128 when catheter system 10 is not being used to withdraw and return blood to a patient. Occluders 64 prevent back flow from the patient or introduction of air into the circulatory system of the patient, and may comprise conventional clips or other such devices for this purpose.

Turning to FIG. 5, the distal end 20 of multi-lumen catheter tube 18 is designed to diminish the mixing of blood flowing into and out of catheter tube 18. To diminish the mixing of blood, the distal end of catheter tube 18 is slanted or beveled so as to form first and second surfaces 66 and 68 that are angled away from one another. As shown in FIG. 5, the distal end of return lumen 24 is disposed flush with first surface 66, and the distal ends 34 and 36 of withdrawal lumens 26 and 28 are disposed flush with second surface 68. Because the first and second surfaces 66 and 68 are angled away from one another, blood returning to the patient through return lumen 24 is directed away from the distal ends 34 and 36 of withdrawal lumens 26 and 28. This helps prevent blood that has been just returned to the patient from being immediately drawn into withdrawal lumens 26 and 28.

In the preferred embodiment, the distal end 20 of catheter 12 has a "V-shape." The bevel on distal end 20, as shown in FIG. 5, is also offset from the center of catheter tube 18 because the withdrawal lumens 26 and 28 extend across the center of catheter tube 18, as seen in FIG. 3. Alternate embodiments of catheter 12 can include a distal end 20 having a curved bevel forming a hyperbolic or otherwise rounded distal end 20. Alternate embodiments of catheter 12 can include further separation of the return and withdrawal lumen elements by terminating the return lumen(s) a distance past the withdrawal lumen(s). This is particularly efficient, because the blood flow in the vein will be in a direction from the withdrawal lumen to the return lumen, so that the blood flowing in the vein will become mixed with the returning blood downstream of the withdrawal lumen.

It has been found that for a catheter insertion on the left upper chest via the left subclavian vein with the distal catheter tip placed at the cavo-atrial junction, a catheter length of 19 to 20 centimeters from the skin site for vein entry ("X" on FIG. 1) plus a suitable length for the subcutaneous tunnel is suitable for virtually all patients. Thus, the catheter is preferably of such length.

Catheter system 10 includes a specialized catheter cutting tool 70 as seen in FIGS. 6 and 7 for cutting catheter 12 at a selected length and to provide precise bevelling of the distal end 20 of catheter 12. Catheter cutting tool 70 includes a catheter holding fixture 72 and a connected blade mounting unit 74.

Catheter holding fixture 72 has a longitudinal passageway 76 sized for catheter tube 18 to be extended therethrough. A slot 78 extends through the fixture 72 and into the longitudinal opening 76. Four posts 80 are attached to the fixture 72 and extend upwards. Posts 80 extend into and are moveable within mating channels 82 formed in blade mounting unit 74. Compression springs 84 surround posts 80 and bias the blade mounting unit 74 away from catheter holding fixture 72.

A blade 86 is mounted to blade mounting unit 74 and is disposed above the slot 78. The shape of blade 86 corresponds with the shape of slot 78 and the desired bevel or slants on the distal end of the catheter tube. To cut a catheter tube 18 and form a bevelled end, blade mounting unit 74 is pressed towards catheter holding fixture 72. This causes the blade to enter through slot 78 and into the longitudinal opening 76 of catheter holding fixture 72 such that catheter 12 is cut by blade 86.

To provide for precise cutting of catheter 12, alignment marks 88 are provided on blade mounting unit 74 and mating alignment marks 90 are provided on catheter tube 18. The catheter cutting tool 70 is rotated about catheter 12 to line-up alignment marks 88 with alignment marks 90. Once aligned, the catheter cutting tool 70 can be used to precisely cut catheter 12. Also, the marks 88 and 90 permit sizing of the length of the catheter tube as selected by the surgeon for patient in which the catheter is to be placed.

In operation, multi-lumen catheter system 10 is used for blood treatment processes such as apheresis. Once catheter 12 has been properly inserted into the patient and the catheter system connected as shown in FIG. 1, the blood treatment process is started by activating pump 14. Pump 14 creates a pulsatile flow of blood both into and out of the patient through the catheter 12.

A vacuum is created on withdrawal lumens 26 and 28 causing blood to be drawn into the distal ends 34 and 36 and through withdrawal lumens 26 and 28. Blood drawn through the withdrawal lumens 26 and 28 is pulled through the pair of external withdrawal lumens 126 and 128. The blood flowing through withdrawal lumens 126 and 128 is merged together by external coupler 46 and directed into attached apheresis withdrawal tube 44. Withdrawal apheresis tube 44 leads to blood treatment device 16 where the withdrawn blood can be processed.

Processed blood is also simultaneously pumped by pump 14 from blood treatment device 16 into external return lumen 124. Blood or fluid in return lumen 124 is pumped under pressure through lumen 24 of catheter tube 18. The pressure of the blood passing through return lumen 24 stiffens catheter tube 18 to help prevent withdrawal lumens 26 and 28 from collapsing.

Blood or fluid flow through the return lumen 24 is directed out of the distal end 32. Distal end 32 is angled away from the distal ends 34 and 36 of the withdrawal lumens 26 and 28 so as to reduce mixing of treated blood with the blood drawn in by withdrawal lumens 26 and 28.

Catheter system 10 simultaneously withdraws blood from the patient and returns processed blood or fluid to the patient at equal flow rates. The withdrawal lumen branch has a flow resistance less than or equal to that of the return lumen so that at the clinically effective flow rates there is not a pressure differential in the withdrawal lumens that would cause them to collapse.

The catheter 12 is capable of sustaining high blood flow rates without the withdrawal lumens 26 and 28 collapsing and failing. This is achieved by using a pair of withdrawal lumens 26 instead of a single, larger withdrawal lumen. The two smaller withdrawal lumens 26 and 28 have less tendency to collapse than single, large lumen because of its higher catheter wall thickness-to-lumen ratio and the shorter span of outer wall between supporting septum walls.

When catheter system 10 is not used for blood treatment procedures such as apheresis, catheter 12 can be used as an indwelling catheter for administering drugs, blood products, and other fluids to the patient or to withdraw aliquots of blood for blood tests. To use catheter 12 to administer drugs, apheresis tubes 42 and 44 and external coupler 46 are disconnected from lumens 124, 126, and 128 as shown in FIG. 4. One or more of lumens 124–128 can then be conventionally connected and used to administer drugs, intravenous feedings or the like. Occluders 64 can be positioned in a closed position to block lumens 24, 26, 28 when they are not in use in order to prevent inadvertent back flow from the patient or introduction of air into the venous system of the patient.

The design confers the ability for long term use. Catheter tube 18 is formed from a biomedical polymer suitable for chronic venous and tissue placement. The diameter of the catheter permits the use of standard procedures for venous placement. A fibrous cuff on catheter tube 18 is a standard feature for tunnelled catheters which diminishes the likelihood of accidental displacement and prevents bacterial migration around catheter tube 18. It is envisioned that the catheter tube 18 will be introduced into the venous system by standard percutaneous methods or by venous cutdown methods. The proximal end of catheter tube 18 will tunnel subcutaneously back from the venous introduction site and exit through a skin incision. The fibrous cuff on proximal catheter can be positioned within the subcutaneous near the catheter skin exit incision. The cuff material is firmly bonded to the catheter and tissue reaction with fibrous ingrowth bonds the catheter to the subcutaneous tissue and establishes a physical barrier to bacterial migration.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A multi-lumen catheter comprising:
a) an elongated cylindrical tube having a distal and a proximal end and a lumen therethrough;
b) a transverse septum extending from the distal end to the proximal end of the tube within the lumen of the tube and dividing the tube into a return passageway and a withdrawal passageway, the withdrawal and return passageways open at the distal and proximal ends of the tube;
c) return septum extending from the distal end to the proximal end of the tube and dividing the return passageway into first and second return lumens; and
d) a supporting septum extending from the distal end to the proximal end of the tube and dividing the withdrawal passageway into first and second withdrawal lumens, the supporting septum supportingly engaging the transverse septum to support the transverse septum and deter deflection of the transverse septum,
wherein the withdrawal lumens have a total cross-sectional area greater than or equal to that of the total cross-sectional area of the return lumens.

2. A multi-lumen catheter comprising:
a) an elongated cylindrical tube having a distal and a proximal end and a lumen therethrough;
b) a transverse septum extending from the distal end to the proximal end of the tube within the lumen of the tube and dividing the tube into a return passageway and a withdrawal passageway, the withdrawal and return passageways open at the distal and proximal ends of the tube;
c) return septum extending from the distal end to the proximal end of the tube and dividing the return passageway into first and second return lumens; and
d) a supporting septum extending from the distal end to the proximal end of the tube and dividing the withdrawal passageway into first and second withdrawal lumens the supporting septum supportingly engaging the transverse septum to support the transverse septum and deter deflection of the transverse septum,
wherein the withdrawal lumens have a combined flow resistance less than or equal to the combined flow resistance of the return lumens so that the total flow rate for blood flowing through the withdrawal lumens does not create a pressure differential sufficient to cause the withdrawal lumens to collapse.

3. A multi-lumen catheter comprising:
a) an elongated cylindrical tube having a distal and a proximal end and a lumen therethrough;
b) a transverse septum extending from the distal end to the proximal end of the tube within the lumen of the tube and dividing the tube into a return passageway and a withdrawal passageway the withdrawal and return passageways open at the distal and proximal ends of the tube; and
c) a supporting septum extending from the distal end to the proximal end of the tube and dividing the withdrawal passageway into first and second withdrawal lumens, the supporting septum supportingly engaging the transverse septum to support the transverse septum and deter deflection of the transverse septum,
wherein the return passageway comprises a single return lumen, and wherein the withdrawal lumens have a total cross-sectional area greater than or equal to that of the return lumen.

4. A multi-lumen catheter comprising:
a) an elongated cylindrical tube having a distal and a proximal end and a lumen therethrough;
b) a transverse septum extending from the distal end to the proximal end of the tube within the lumen of the tube and dividing the tube into a return passageway and a withdrawal passageway, the withdrawal and return passageways open at the distal and proximal ends of the tube; and
c) a supporting septum extending from the distal end to the proximal end of the tube and dividing the withdrawal passageway into first and second withdrawal lumens, the supporting septum supportingly engaging the transverse septum to support the transverse septum and deter deflection of the transverse septum,
wherein the return passageway comprises a single return lumen, and wherein the withdrawal lumens have a combined flow resistance less than or equal to the flow resistance of the return lumen so that the total flow rate for blood flowing through the withdrawal lumens does not create a pressure differential sufficient to cause the withdrawal lumens to collapse.

5. A multi-lumen catheter comprising:
a) an elongated cylindrical tube having a distal and a proximal end and a lumen therethrough, said distal end of the tube having a first beveled surface and a second beveled surface angled away from the first beveled surface;
b) a transverse septum extending from the distal end to the proximal end of the tube within the lumen of the tube and dividing the tube into a withdrawal passageway and a return passageway, the withdrawal passageway open at the first beveled surface at the distal end of the tube, and the return passageway open at the second beveled surface at the distal end of the tube; and
c) a return septum extending from the distal end to the proximal end of the tube and dividing the return passageway into first and second return lumens,
wherein the withdrawal lumens have a total cross-sectional area greater than or equal to that of the total cross-sectional area of the return lumens.

6. A multi-lumen catheter comprising:
a) an elongated cylindrical tube having a distal and a proximal end and a lumen therethrough said distal end of the tube having a first beveled surface and a second beveled surface angled away from the first beveled surface:
b) a transverse septum extending from the distal end to the proximal end of the tube within the lumen of the tube and dividing the tube into a withdrawal passageway and a return passageway, the withdrawal passageway open at the first beveled surface at the distal end of the tube, and the return passageway open at the second beveled surface at the distal end of the tube; and c) a return septum extending from the distal end to the proximal end of the tube and dividing the return passageway into first and second return lumens, wherein the withdrawal lumens have a combined flow resistance less than or equal to the combined flow resistance of the return lumens so that the total flow rate for blood flowing through the withdrawal lumens does not create a pressure differential sufficient to cause the withdrawal lumens to collapse.

7. A multi-lumen catheter comprising:

an elongated cylindrical tube having a distal and a proximal end and a lumen therethrough, said distal end of the tube having a first beveled surface and a second beveled surface angled away from the first beveled surface; and b) a transverse septum extending from the distal end to the proximal end of the tube within the lumen of the tube and dividing the tube into a withdrawal passageway and a return passageway the withdrawal passageway open at the first beveled surface at the distal end of the tube, and the return passageway open at the second beveled surface at the distal end of the tube, wherein the return passageway comprises a single return lumen and wherein the withdrawal lumens have a total cross-sectional area greater than or equal to that of the return lumen.

8. A multi-lumen catheter comprising:

a) an elongated cylindrical tube having a distal and a proximal end and a lumen therethrough said distal end of the tube having a first beveled surface and a second beveled surface angled away from the first beveled surface; and b) a transverse septum extending from the distal end to the proximal end of the tube within the lumen of the tube and dividing the tube into a withdrawal passageway and a return passageway, the withdrawal passageway open at the first beveled surface at the distal end of the tube, and the return passageway open at the second beveled surface at the distal end of the tube, wherein the return passageway comprises a single return lumen and wherein the withdrawal lumens have a combined flow resistance less than or equal to the flow resistance of the return lumen so that the total flow rate for blood flowing through the withdrawal lumens does not create a pressure differential sufficient to cause the withdrawal lumens to collapse.

9. A multi-lumen catheter comprising:

a) an elongated cylindrical tube having a distal and a proximal end and a lumen therethrough;

b) a transverse septum extending from the distal end to the proximal end of the tube within the lumen and dividing the tube into a return passageway for carrying fluid at first pressure and a withdrawal passageway for carrying fluid at a second pressure, said first and second pressures creating a pressure differential across said transverse septum;

c) a supporting septum engaging said transverse septum and restraining said transverse septum against deflection in response to said pressure differential to substantially prevent collapsing of the transverse septum into the withdrawal passageway; and d) a return septum extending from the distal end to the proximal end of the tube and dividing the return passageway into first and second return lumens, wherein the withdrawal lumens have a total cross-sectional area greater than or equal to the total cross-sectional area of the return lumens.

10. A multi-lumen catheter comprising:

a) an elongated cylindrical tube having a distal and a proximal end and a lumen therethrough;

b) a transverse septum extending from the distal end to the proximal end of the tube within the lumen and dividing the tube into a return passageway for carrying fluid at first pressure, and a withdrawal passageway for carrying fluid at a second pressure, said first and second pressures creating a pressure differential across said transverse septum;

c) a supporting septum engaging said transverse septum and restraining said transverse septum against deflection in response to said pressure differential to substantially prevent collapsing of the transverse septum into the withdrawal passageway; and d) a return septum extending from the distal end to the proximal end of the tube and dividing the return passageway into first and second return lumens, wherein the withdrawal lumens have a combined flow resistance less than or equal to the combined flow resistance of the return lumens.

11. A multi-lumen catheter comprising:

a) an elongated cylindrical tube having a distal and a proximal end and a lumen therethrough;

b) a transverse septum extending from the distal end to the proximal end of the tube within the lumen and dividing the tube into a return passageway for carrying fluid at first pressure, and a withdrawal passageway for carrying fluid at a second pressure, said first and second pressures creating a pressure differential across said transverse septum; and c) a supporting septum engaging said transverse septum and restraining said transverse septum against deflection in response to said pressure differential to substantially prevent collapsing of the transverse septum into the withdrawal passageway, wherein the return passageway comprises a single return lumen, and wherein the withdrawal lumens have a total cross-sectional area greater than or equal to the total cross-sectional area of the return lumen.

12. A multi-lumen catheter comprising:

a) an elongated cylindrical tube having a distal and a proximal end and a lumen therethrough;

b) a transverse septum extending from the distal end to the proximal end of the tube within the lumen and dividing the tube into a return passageway for carrying fluid at first pressure, and a withdrawal passageway for carrying fluid at a second pressure, said first and second pressures creating a pressure differential across said transverse septum; and c) a supporting septum engaging said transverse septum and restraining said transverse septum against deflection in response to said pressure differential to substantially prevent collapsing of the transverse septum into the withdrawal passageway, wherein the return passageway comprises a single return lumen and wherein the withdrawal lumens have a combined flow resistance less than or equal to the flow resistance of the return lumen.

* * * * *